United States Patent
Nelson, Jr. et al.

(10) Patent No.: US 12,339,220 B2
(45) Date of Patent: Jun. 24, 2025

(54) RAPID, SENSITIVE HYDROGEN DETECTOR WITH FLOW PATH DIFFERENCE COMPENSATION

(71) Applicant: Aerodyne Research, Inc., Billerica, MA (US)

(72) Inventors: David D. Nelson, Jr., N. Chelmsford, MA (US); Scott C. Herndon, Littleton, MA (US); Joanne H. Shorter, Lexington, MA (US); Joseph R. Roscioli, Chelmsford, MA (US)

(73) Assignee: Aerodyne Research, Inc., Billerica, MA (US)

( * ) Notice: Subject to any disclaimer, the term of this patent is extended or adjusted under 35 U.S.C. 154(b) by 359 days.

(21) Appl. No.: 18/099,468

(22) Filed: Jan. 20, 2023

(65) Prior Publication Data
US 2023/0152220 A1    May 18, 2023

Related U.S. Application Data

(63) Continuation-in-part of application No. 17/178,696, filed on Feb. 18, 2021, now Pat. No. 11,802,858.

(51) Int. Cl.
*G01N 21/3504* (2014.01)
*G01N 31/00* (2006.01)
*G01N 33/00* (2006.01)

(52) U.S. Cl.
CPC ....... *G01N 21/3504* (2013.01); *G01N 31/007* (2013.01); *G01N 33/0013* (2013.01)

(58) Field of Classification Search
CPC ............. G01N 21/3504; G01N 31/007; G01N 33/0013; G01N 2021/1789; G01N 21/3554; G01N 33/005; G01N 33/006
See application file for complete search history.

(56) References Cited

U.S. PATENT DOCUMENTS

| | | |
|---|---|---|
| 3,549,327 A | 12/1970 | Fergusson |
| 6,897,960 B2 | 5/2005 | DiMeo, Jr. et al. |

(Continued)

FOREIGN PATENT DOCUMENTS

| | | |
|---|---|---|
| CN | 201811870 U | 4/2011 |
| CN | 111007031 A | 4/2020 |

(Continued)

OTHER PUBLICATIONS

WO-2013005332-A1 (Year: 2013).*
Chtanov, A., et al., "Differential Optical Detection of Hydrogen Gas in the Atmosphere," Elsevier Sciences B.V., Elsevier, Sensors and Actuators, vol. 79, Issue 2-3, Oct. 15, 2001, pp. 196-199.

(Continued)

*Primary Examiner* — Kristina M Deherrera
*Assistant Examiner* — Fatemeh Esfandiari Nia
(74) *Attorney, Agent, or Firm* — Cesari and McKenna, LLP; James A. Blanchette

(57) ABSTRACT

In various embodiments, rapid, sensitive detection of molecular hydrogen is achieved by in a detector that divides sample gas into two flows by dividing the sample gas before dampening variation and converting hydrogen to water vapor at two different points. For example, a detector may receive sample gas that includes ambient water vapor and hydrogen, divide the sample gas into a chemical conversion flow and bypass flow, perform a first chemical conversion of hydrogen in the chemical conversion flow to water vapor, alternate between drying the converted chemical conversion flow or the bypass flow to produce a modulated flow, perform a second chemical conversion of hydrogen in the modulated flow to water vapor, measure water vapor in the converted modulated flow to produce a water vapor signal, separate the water vapor signal in the time domain to extract a hydrogen-derived water vapor signal, and output a hydrogen signal based thereon.

20 Claims, 8 Drawing Sheets

(56) References Cited

U.S. PATENT DOCUMENTS

| | | | |
|---|---|---|---|
| 7,255,836 | B2 | 8/2007 | Lehmann et al. |
| 7,277,177 | B2 | 10/2007 | Augustine et al. |
| 7,852,480 | B2 | 12/2010 | Uchiyama |
| 8,448,493 | B2 | 5/2013 | McIntyre et al. |
| 9,322,969 | B2 | 4/2016 | Burov et al. |
| 11,561,324 | B1 | 1/2023 | Burba |
| 11,802,858 | B2 | 10/2023 | Nelson, Jr. et al. |
| 2002/0154310 | A1 | 10/2002 | DiMeo, Jr. et al. |
| 2003/0082417 | A1 | 5/2003 | Lillis |
| 2004/0023595 | A1 | 2/2004 | Ping et al. |
| 2004/0107764 | A1 | 6/2004 | Yan |
| 2004/0193379 | A1 | 9/2004 | Lillis et al. |
| 2005/0272167 | A1 | 12/2005 | Andino |
| 2007/0240488 | A1 | 10/2007 | Kreuser et al. |
| 2011/0174052 | A1 | 7/2011 | Kuebel |
| 2013/0059395 | A1 * | 3/2013 | Alvarez ............... G01N 21/39 |
| | | | 436/101 |
| 2017/0023475 | A1 | 1/2017 | Dam et al. |
| 2017/0184537 | A1 | 6/2017 | Umasankar et al. |
| 2019/0263699 | A1 | 8/2019 | Finger et al. |
| 2019/0391045 | A1 | 12/2019 | Yoshimura |
| 2020/0033301 | A1 | 1/2020 | Cardin |
| 2020/0249184 | A1 | 8/2020 | Matsukura et al. |
| 2021/0293768 | A1 | 9/2021 | Johnson et al. |
| 2022/0187203 | A1 | 6/2022 | Zondlo et al. |
| 2022/0260537 | A1 | 8/2022 | Nelson, Jr. et al. |
| 2023/0116043 | A1 | 4/2023 | Nelson, Jr. et al. |
| 2024/0094178 | A1 | 3/2024 | Nelson, Jr. et al. |

FOREIGN PATENT DOCUMENTS

| | | | |
|---|---|---|---|
| CN | 108562017 | B | 11/2020 |
| EP | 2140249 | B1 | 9/2011 |
| GB | 1017940 | A | 1/1966 |
| JP | S-49-026920 | B1 | 7/1974 |
| JP | S60-80755 | A | 5/1985 |
| JP | H07-325075 | A | 12/1995 |
| JP | 2006-179224 | A | 7/2006 |
| JP | 2011-257319 | A | 12/2011 |
| JP | 6641218 | B2 | 2/2020 |
| WO | 2011/155086 | A1 | 12/2011 |
| WO | WO-2013005332 | A1 * | 1/2013 ......... G01N 21/3504 |
| WO | WO-2020/172541 | A1 | 8/2020 |

OTHER PUBLICATIONS

"HALO H2: Trace-Level Hydrogen Analyzer," Tiger Optics, Tiger Optics, LLC, May 2020, pp. 1-2.

"HALO H2: Trace-Level Hydrogen Analyzer," Tiger Optics, Tiger Optics, LLC, Oct. 2021, pp. 1-2.

L'vov, Boris V., et al., "Catalytic Oxidation of Hydrogen on Platinum," Springer, Akadémiai Kiadó, Budapest Hungary, Journal of Thermal Analysis Calorimetry, Sep. 7, 2012, pp. 1-8.

"Notification of Transmittal of the International Search Report and the Written Opinion of the International Searching Authority, or the Declaration," International Filing Date: Jan. 27, 2022, International Application No. PCT/US2022/014073, Applicant: Aerodyne Research, Inc., Date of Mailing: Jun. 21, 2022, pp. 1-19.

Rizzolo, Serena, et al., "Distributed and Discrete Hydrogen Monitoring Through Optical Fiber Sensors Based on Optical Frequency Domain Reflectometry," IOP Publishing Ltd, JPhys Photonics, vol. 2, Jan. 28, 2020, pp. 1-7.

Rollins, A. W., et al., "Catalytic Oxidation of $H_2$ on Platinum: A robust Method for Generating Low Mixing Ratio $H_2O$ Standards," Copernicus Publications, Atmospheric Measurement Techniques, vol. 4, Oct. 4, 2011, pp. 2059-2064.

Shin, Woosuck et al., "Hydrogen-Selective Thermoelectric Gas Sensor", Sensors an Actuators B: Chemical, Elsevier B.V., NL, vol. 93, No. 1-3, Aug. 1, 2003, pp. 304-308.

Shin, Woosuck et al., "Integration of Ceramic Catalyst on Micro-Thermoelectric Gas Sensor", Sensors an Actuators B: Chemical, Elsevier B.V., NL, vol. 118, No. 1-2, Oct. 25, 2006, pp. 283-291.

CN-108562017-B-eng (Year: 2020).

JP-6641218-B2-eng (Year: 2020).

"Notification of Transmittal of the International Search Report and the Written Opinion of the International Searching Authority, or the Declaration," International Filing Date: Oct. 31, 2023, International Application No. PCT/US2023/036493, Date of Mailing: Feb. 26, 2024, pp. 1-12.

"Notification of Transmittal of the International Search Report and the Written Opinion of the International Searching Authority, or the Declaration," International Filing Date: Nov. 6, 2024, International Application No. PCT/US2024/054734, Date of Mailing: Jan. 27, 2025, pp. 1-13.

English Translation of CN-201811870-U (Year: 2011).

* cited by examiner

RAPID, SENSITIVE HYDROGEN DETECTOR WITH FLOW PATH DIFFERENCE COMPENSATION

RELATED APPLICATIONS

The present application is a continuation-in-part of U.S. patent application Ser. No. 17/178,696, filed on Feb. 18, 2021, by David D. Nelson, Jr. et al for a "Rapid, Sensitive Hydrogen Detector", the contents of which are incorporated by reference herein in their entirety, now issued as U.S. Pat. No. 11,802,858.

BACKGROUND

Technical Field

The present disclosure relates generally to gas detection, and more particularly to rapid, sensitive detection of molecular hydrogen.

Background Information

There is a growing need for rapid, sensitive detection of molecular hydrogen. As the world transitions away from fossil fuels as our primary energy source, it is likely that a hydrogen-based energy infrastructure will emerge. Both for economic and safety reasons it will be essential to have effective ways of measuring hydrogen concentration. For example, to detect hydrogen gas leaks it will be essential to have effective ways of measuring hydrogen concentration in sample gas (e.g., atmospheric air). Just as methane detectors play an important role in our existing natural gas-based energy infrastructure, hydrogen detectors will likely play an important role in hydrogen-based energy infrastructure.

Many currently deployed methane detectors utilize optical detection to measure methane concentration and detect methane gas leaks. Optical detection can be fast, sensitive, portable, and specific, and it would seemingly be an appealing option for use in detecting hydrogen. However, unlike methane, hydrogen has no strong absorption features in the near ultraviolet (UV), visible, infrared (IR) or microwave regions of the electromagnetic spectrum. Accordingly, it is very difficult to optically detect hydrogen molecules with conventional techniques and direct optical detectors for hydrogen have not proved viable.

Accordingly, there is a need for improved techniques for detecting molecular hydrogen that may enable rapid, sensitive hydrogen detection.

SUMMARY

In various embodiments, rapid, sensitive detection of molecular hydrogen is achieved by chemically converting hydrogen to water vapor (i.e., oxidizing the hydrogen) and then optically detecting the water vapor (e.g., using an optical detection technique such as laser spectroscopy, non-dispersive infrared (NDIR) absorption spectroscopy, etc.). The water vapor serves as a surrogate for hydrogen, such that hydrogen is indirectly detected. Indirect detection avoids the difficulties of optically detecting hydrogen molecules themselves and may provide other advantages. However, indirect detection may also introduce other challenges. In various embodiments described herein, these other challenges may be addressed.

One challenge is that the sample gas (e.g., atmospheric air) often includes significant ambient water vapor (e.g., 1% to 4%). The additional water vapor produced by chemically converting hydrogen will typically be very small compared to the ambient water vapor. Even when detecting nearby a hydrogen leak it may be hundreds of times smaller, and if remote from a hydrogen leak it may be tens of thousands of times smaller. In addition, the amount of ambient water vapor may change with time, and be correlated with air movements, causing further problems in specific detection.

In various embodiments described herein, this challenge may be addressed by separating a water vapor signal describing detected water vapor concentration into two components in the time domain, referred to as the "ambient water vapor signal" and the "hydrogen-derived water vapor signal." Separation may be facilitated by dampening variation in the ambient water vapor signal to differentiate it from the more rapidly varying hydrogen-derived water vapor signal. Dampening may be achieved in various manners. In one embodiment, a gas dryer (e.g., a Nafion® sulfonated tetrafluoroethylene based fluoropolymer-copolymer membrane gas dryer) may be employed.

Various additional techniques may be employed to enhance such embodiments. In one embodiment, the detection may be enhanced by dampening variation in ambient water vapor and rapidly actively modulating the hydrogen-derived water vapor signal. After dampening variation in the ambient water vapor signal (e.g., by passing the sample gas through a gas dryer), the sample gas may be divided into a chemical conversion flow and a bypass flow. Hydrogen in the chemical conversion flow is converted to water vapor (e.g., in a catalytic oven). Water vapor measurements are alternated between the converted chemical conversion flow or the bypass flow to produce a water vapor signal. The alternating actively modulates the hydrogen-derived component of the water vapor signal facilitating separation of the hydrogen-derived water vapor signal from the water vapor signal.

However, additional challenges may be encountered in embodiments that divide sample gas into a chemical conversion flow and a bypass flow. One challenge that may be encountered is minute differences in the paths of the chemical conversion flow and the bypass flow, caused by leaks, differing amounts of water adsorption or desorption on surfaces, or other factors. If the paths were absolutely identical, the water vapor signal resulting from flow through each path should be identical, such that in the absence of hydrogen in the sample gas a differential signal measuring difference in water vapor concentration of flow through each path should be zero. However, in practice there is often a non-zero differential signal (i.e., an offset).

In one embodiment, such offset may be addressed by dividing the sample gas into a chemical conversion flow and a bypass flow before dampening variation (e.g., by passing through a gas dryer) and converting hydrogen to water vapor at two different points (e.g., using two catalytic ovens), one disposed before the dampening and one after. In such an arrangement, any non-zero differential signal (i.e., offset) may be erased by the first conversion of hydrogen to water vapor (e.g., in a first catalytic oven) and dampening (e.g., passing through the gas dryer). This may also erase any hydrogen-derived water vapor signal produced by the first chemical conversion. A hydrogen-derived water vapor signal may be recovered by performing a second conversion of hydrogen to water vapor (e.g., in a second catalytic oven). Measurement of water vapor from this second conversion may be used to indirectly detect hydrogen in the sample gas.

It should be understood that a variety of additional features and embodiments may be implemented other than those discussed in this Summary. This Summary is intended simply as a brief introduction to the reader for the further description that follows, and does not indicate or imply that the features and embodiments mentioned herein cover all aspects of the disclosure, or are necessary or essential parts of the disclosure.

BRIEF DESCRIPTION OF THE DRAWINGS

The description refers to the accompanying drawings of example embodiments, of which.

DETAILED DESCRIPTION OF ILLUSTRATIVE EMBODIMENTS

Figure 1A:
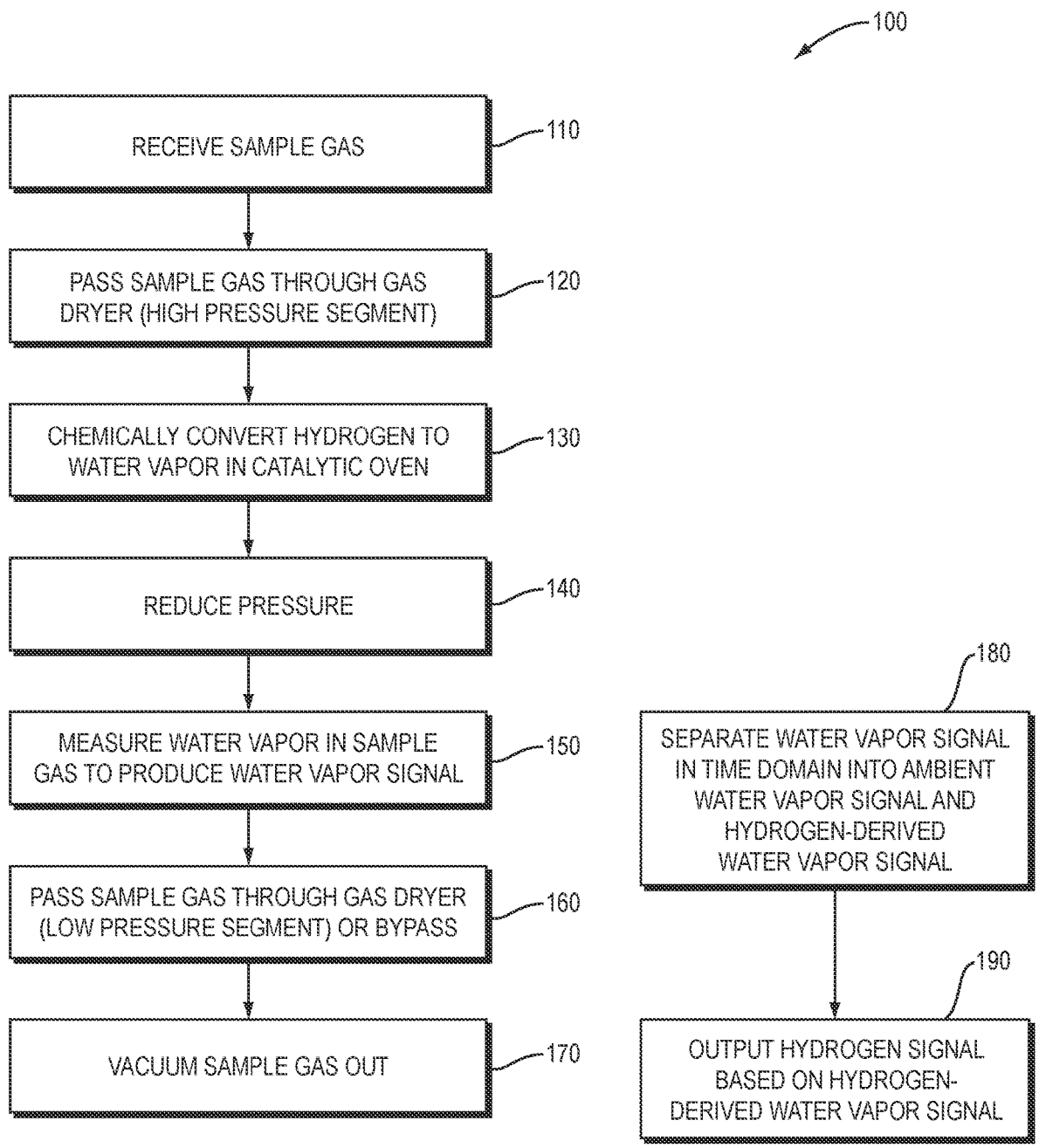
FIG. 1A is a flow diagram of an example sequence of steps for detecting molecular hydrogen according to a first embodiment.
Figure 1B:
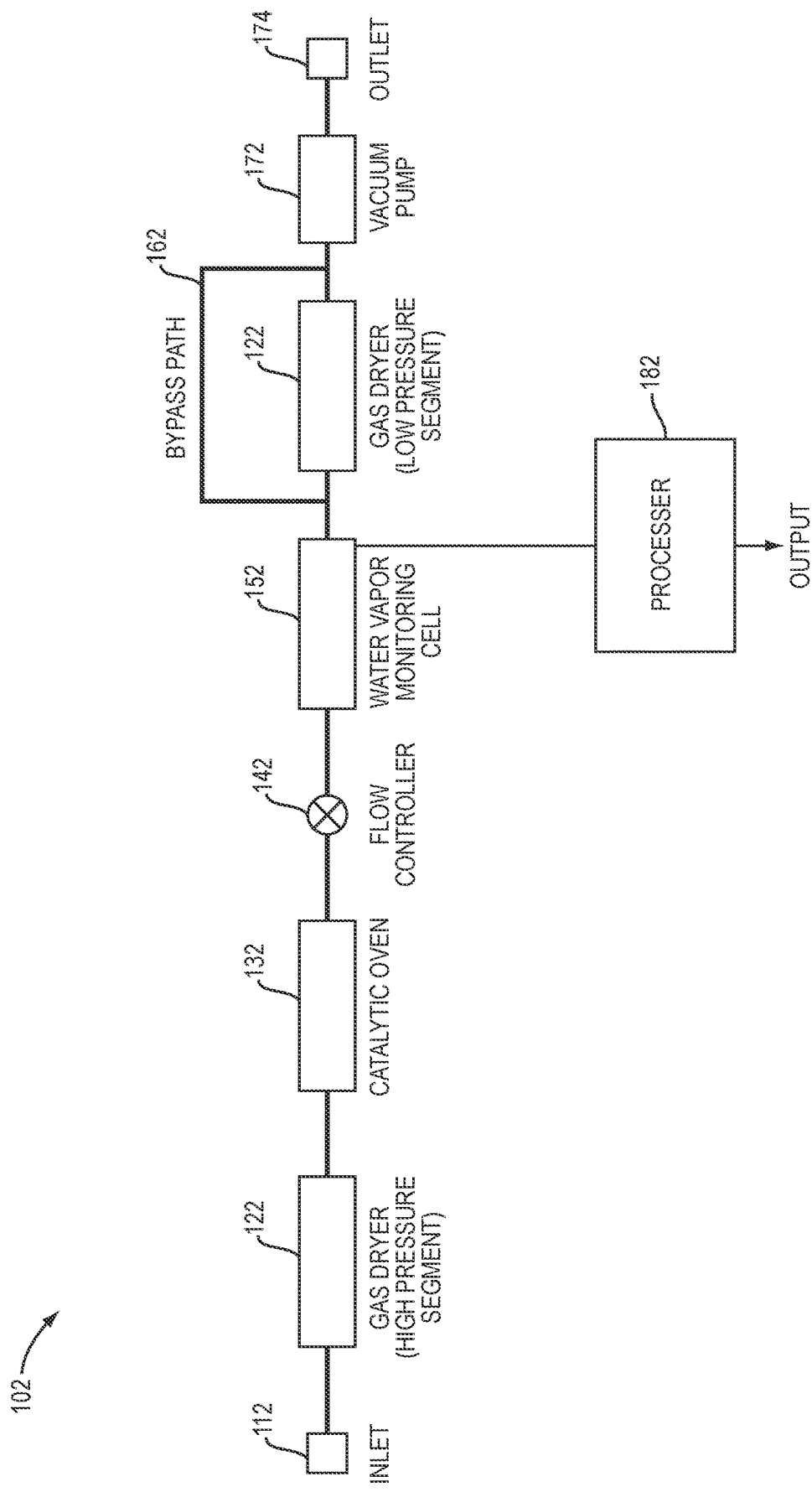
FIG. 1B is a block diagram of an example hydrogen detector with components that may implement the sequence of steps in FIG. 1A.

FIG. 1A is a flow diagram of an example sequence of steps 100 for detecting molecular hydrogen according to a first embodiment. FIG. 1B is a block diagram of an example hydrogen detector 102 with components that may implement the sequence of steps 100 in FIG. 1A. At step 110, an inlet 112 of the hydrogen detector 102 receives sample gas (e.g., atmospheric air) that includes ambient water vapor, molecular hydrogen and potentially hydrogen bearing molecules (including methane and non-methane hydrocarbons (NMHCs)). Ambient water vapor in the sample gas may vary, typically falling between 10,000 and 20,000 ppm for atmospheric air. Hydrogen bearing molecules in the sample gas are typically present in far smaller quantities, typically being about 3 ppm for atmospheric air (methane usually accounting for about 2 ppm and NMHCs accounting for the remaining 1 ppm). Absent a hydrogen source (e.g., a hydrogen leak), hydrogen typically is found at about 0.5 ppm in atmospheric air. A simple implementation of the hydrogen detector 102 may be suited for detecting hydrogen concentrations of about 1 ppm to about 40,000 ppm (i.e., the lower explosive limit of hydrogen). More complicated implementations of the hydrogen detector (e.g., that account for the potential presence of hydrogen bearing molecules in the sample gas) may be capable of specifically detecting sub-1 ppm concentrations.

At step 120, the sample gas from the inlet 112 is passed through a gas dryer 122, or more specifically a high-pressure segment thereof. In one implementation the gas dryer 122 is a Nafion® sulfonated tetrafluoroethylene based fluoropolymer-copolymer membrane gas dryer. Alternatively, a variety of different types of gas dryer may be employed. The gas dryer 122 may remove some ambient water vapor from the sample gas. However, the primary purpose of the gas dryer 122 is not to remove ambient water vapor, but to instead dampen time response in ambient water vapor, while having little effect on hydrogen. As explained further below, the gas dryer 122 serves a role similar to a low pass filter in the field of electronics.

At step 130, sample gas from the gas dryer 122 (or more specifically the high-pressure segment thereof) is received at a catalytic oven 132, which chemically converts hydrogen in the sample gas to water vapor (i.e., oxidizes the hydrogen). The catalytic oven 132 may include a hot (e.g., 100 to 200° Celsius (C.)) catalytic surface (e.g., a platinum (Pt) surface) that rapidly and quantitatively converts hydrogen to water vapor.

The gas dryer 122 and catalytic oven 132 may operate near atmospheric pressure. At step 140, the converted sample gas from the catalytic oven 132 is passed through a flow controller 142 that reduces pressure. The flow controller 142 may cause a pressure drop by limiting flow in various manners. In one implementation, the flow controller is a critical orifice that limits flow. In some cases (e.g., cases with 40,000 ppm or greater water vapor concentrations) condensation may be prone to occur between the catalytic oven 132 and the flow controller 142. To avoid condensation, this region may be maintained at an elevated temperature (e.g., 30° C. or greater). In one implementation, this elevated temperature may be achieved by placing the flow controller 142 very close to the catalytic oven 132 so that byproduct heat from the catalytic oven 132 maintains the elevated temperature.

At step 150, the converted sample gas from the flow controller 142 is received by a water vapor monitoring cell 152, which measures water vapor therein to produce a water vapor signal. The water vapor monitoring cell 152 may employ optical detection, for example, laser spectroscopy or non-dispersive infrared (NDIR) absorption spectroscopy. It should be understood, however, that other types of detection, including other types of optical detection, may be employed, and the water vapor monitoring cell 152 may include various types of devices, including other types of spectrometers.

Figure 1C:
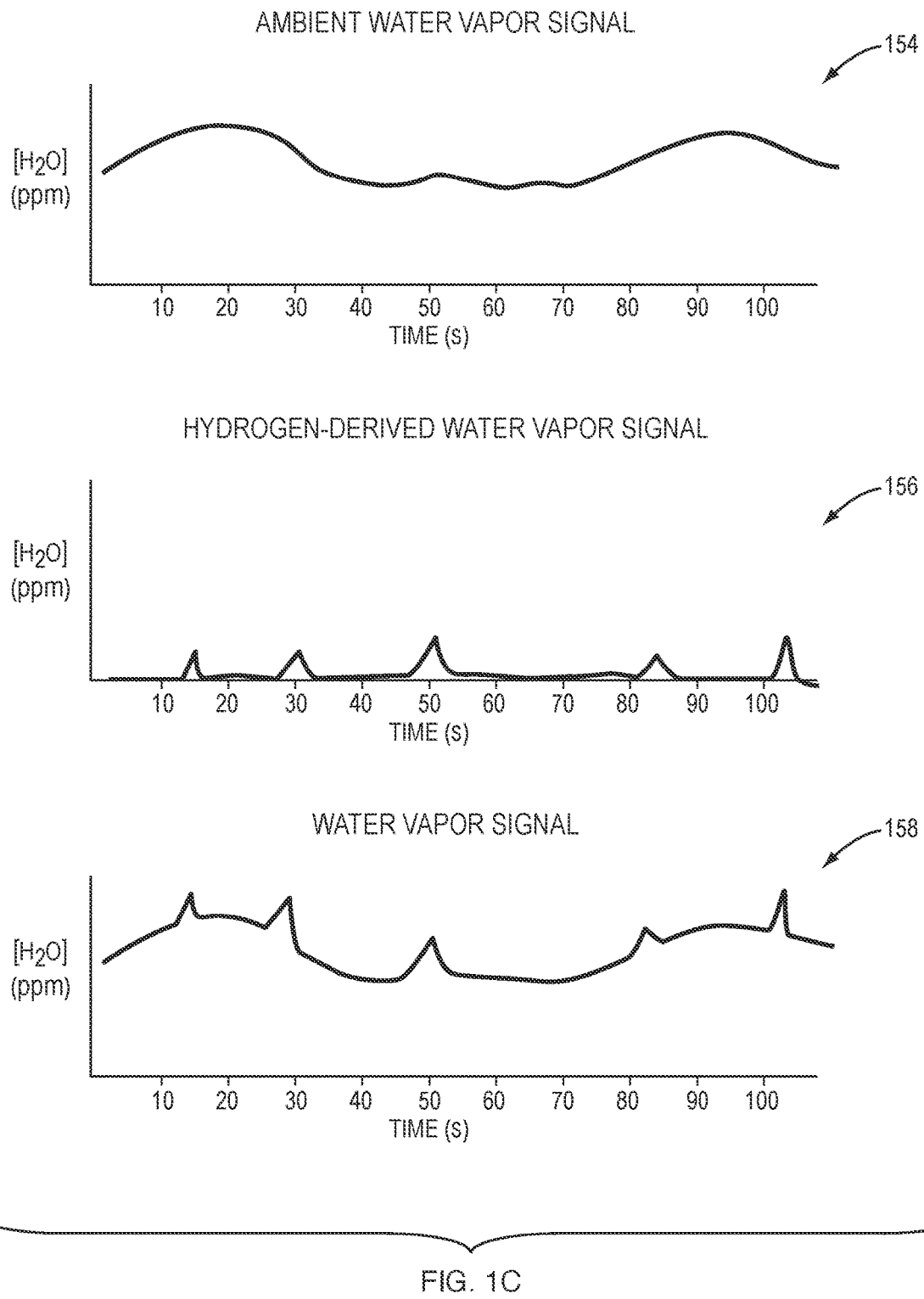
FIG. 1C is a set of graphs 154-158 illustrating an example water vapor signal, ambient water vapor signal and hydrogen-derived water vapor signal as a function of time.

The water vapor signal produced by the water vapor monitoring cell 152 includes two components in the time domain: a component derived from ambient water vapor referred to herein as the "ambient water vapor signal" and a component derived from converted hydrogen referred to herein as the "hydrogen-derived water vapor signal." FIG. 1C is a set of graphs 154-158 illustrating an example water vapor signal, ambient water vapor signal and hydrogen-derived water vapor signal as a function of time. The ambient water vapor signal often has a significant offset (e.g., 100 to 1000 pm) even after reduction by the gas dryer 122 due to the typically large (e.g., 10,000, 20,000 ppm, etc.) concentrations of ambient water vapor in atmospheric air, and typically only varies over long time periods (e.g., time periods greater than a minute). The ambient water vapor signal typically is relatively constant over short time periods (e.g., time periods of less than 1 second (s)) due to the dampening effects of the gas dryer 122. The hydrogen-derived water vapor signal typically has no significant offset due to the typically tiny (e.g., 0.5 ppm) concentrations of hydrogen in atmospheric air (absent a hydrogen source, such as a hydrogen leak). The hydrogen-derived water vapor signal may vary over short time periods (e.g., time periods of less than 1 s) since it is unaffected by the gas dryer 122.

It may be noted that any leaks in the system between the gas dryer 122 (or more specifically the high-pressure segment thereof) and the water vapor monitoring cell 152 may introduce water vapor changes that would not be dampened. Accordingly, special measures may be taken to minimize and/or eliminate potential leaks in this region (e.g., using high quality vacuum plumbing components in this region).

At step 160, the converted sample gas leaves the water vapor monitoring cell 152 and passes again through the gas dryer 122, or more specifically the low-pressure segment thereof. An optional bypass path 162 may also be provided to avoid the low-pressure segment.

At step 170, the converted sample gas passes through a vacuum pump 172 that pulls the sample gas through the hydrogen detector 102 and out an outlet 174.

In parallel, at step 180, the water vapor signal from the water vapor monitoring cell 152 is received by a processor 182 that separates the water vapor signal in the time domain into the ambient water vapor signal and the hydrogen-derived water vapor signal, for example, using digital signal processing (DSP) techniques. The processor 182 determines a hydrogen signal that describes molecular hydrogen in the sample gas based on the hydrogen-derived water vapor signal. In some implementations, the hydrogen-derived water vapor signal may be simply used as the hydrogen signal. In more complicated implementations, a conversion process may be employed to account for sources or errors or other factors.

Finally, at step 190, the processor 182, outputs the hydrogen signal, for example, storing it in a memory, passing it to another instrument, using it to generate a display in a user-interface of the hydrogen detector 102 itself, etc.

Figure 2A:
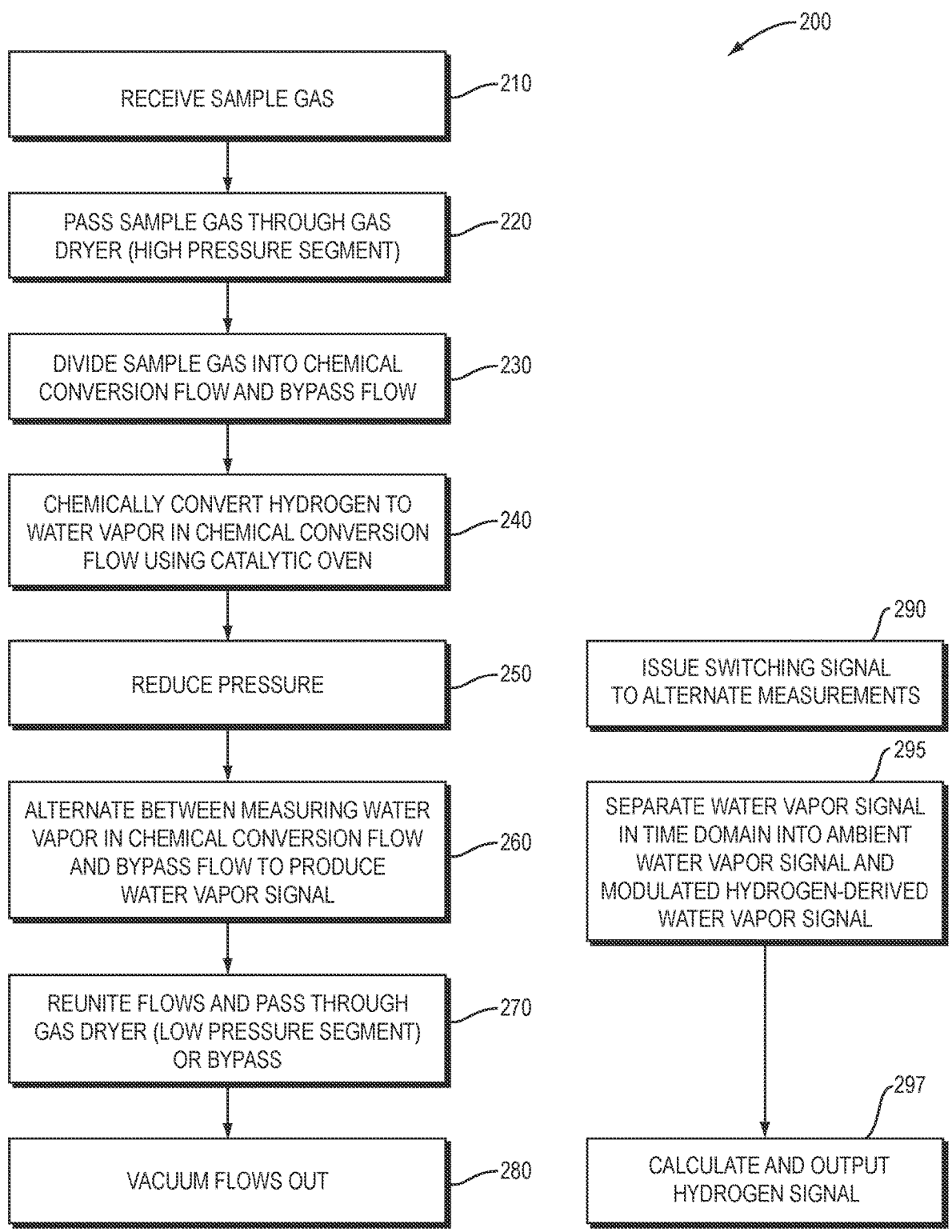
FIG. 2A is a flow diagram of an example sequence of steps for detecting molecular hydrogen according to a second embodiment.
Figure 2B:
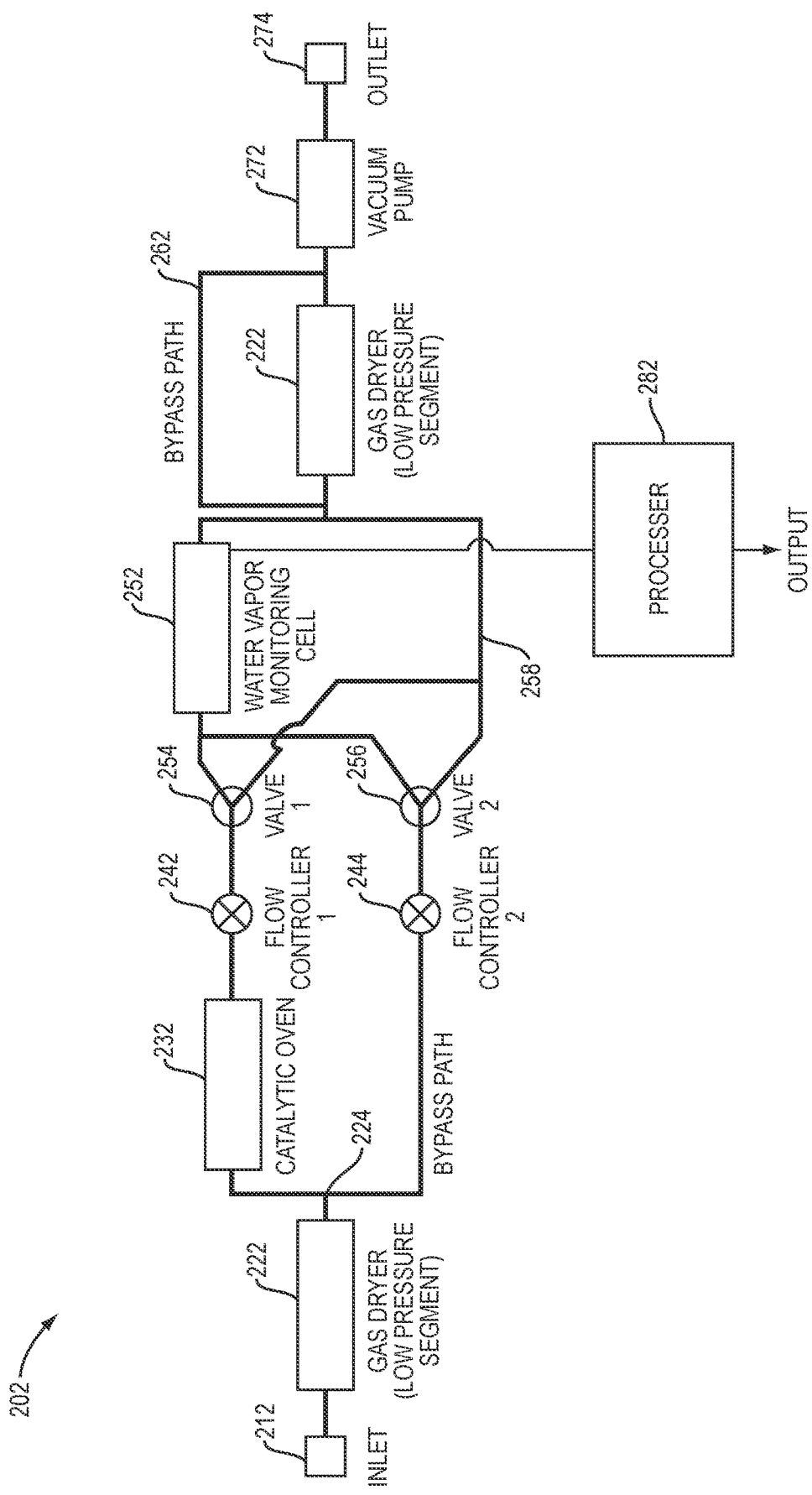
FIG. 2B is a block diagram of an example hydrogen detector with components that may implement the sequence of steps in FIG. 2A.

Performance of the example hydrogen detector 102 discussed in relation to FIGS. 1A-1B may be improved by actively modulating the hydrogen-derived water vapor signal. FIG. 2A is a flow diagram of an example sequence of steps 200 for detecting molecular hydrogen according to a second embodiment. FIG. 2B is a block diagram of an example hydrogen detector 202 with components that may implement the sequence of steps 200 in FIG. 2A. Where the steps and components of FIGS. 2A-2B are similar to those of FIGS. 1A-1B they will be discussed again only briefly, and the reader is referred to the above discussion for more detail.

At step 210, an inlet 212 of the hydrogen detector 202 receives sample gas (e.g., atmospheric air) that includes ambient water vapor, molecular hydrogen and potentially hydrogen bearing molecules (including methane and NMHCs).

At step 220, the sample gas from the inlet 212 is passed through a gas dryer 222, or more specifically a high-pressure segment thereof. Again, the gas dryer 222 may be a Nafion® sulfonated tetrafluoroethylene based fluoropolymer-copolymer membrane gas dryer or another type of dryer, and its primary purpose may be to dampen time response of ambient water vapor, while having little effect on hydrogen.

At step 230, sample gas from the gas dryer 222 (or more specifically the high-pressure segment thereof) is passed to a flow divider 224 that divides the sample gas in half, creating a first flow that is passed to the catalytic oven 232 and that is referred to herein as the "chemical conversion flow," and a second flow that bypasses the catalytic oven 232 and that is referred to herein as the "bypass flow."

At step 240, the catalytic oven 232 chemically converts hydrogen in the chemical conversion flow to water vapor.

Again, the catalytic oven 232 may include a hot (e.g., 200° C.) catalytic surface (e.g., a Pt surface) that rapidly and quantitatively converts hydrogen to water vapor. The gas dryer 222 and catalytic oven 232 may operate near atmospheric pressure.

At step 250, the chemical conversion flow from the catalytic oven 232 is passed through a first flow controller 242 that reduces its pressure, and the bypass flow is passed through a second flow controller 244 that reduces its pressure. Again, to avoid water condensation these regions may be maintained at an elevated temperature (e.g., 30° C. or greater).

At step 260, the water vapor monitoring cell 252 alternates between measuring water vapor in just the chemical conversion flow and in just the bypass flow to produce the water vapor signal. Again, the water vapor monitoring cell 252 may employ optical detection, for example, laser spectroscopy or NDIR absorption spectroscopy. To alternate measurement, first and second valves (e.g., electronically-controlled three-way valves) 254, 256 may be employed. In one implementation, the first valve 254 receives the chemical conversion flow from the first flow controller 242 and directs it either to the water vapor monitoring cell 252 (in its resting state) or to a bypass 258 around the water vapor monitoring cell 252 (in its activated state). The second valve 256 receives the bypass flow from the second flow controller 244 and directs it either around the water vapor monitoring cell 252 (in its resting state) or to the water vapor monitoring cell 252 (in its activated state).

In parallel steps, at step 290, a processor 282 is configured to issue a switching signal (e.g., a square wave) to the first and second valves 254, 256 to activate and deactivate them. The arrangement may maintain flow through the water vapor monitoring cell 252 and the bypass 258 around the water vapor monitoring cell 252 at all times, while alternating between the vapor monitoring cell 252 measuring water vapor in the chemical conversion flow or in the bypass flow. Provided the first and second valves 254, 256 are switched simultaneously, pressure in the vapor monitoring cell 252 will not significantly change, avoiding transient signals from the switching process itself. Further, flow rates through the water vapor monitoring cell 252 and the bypass 258 around the water vapor monitoring cell 252 need not be perfectly matched since their sum is constant and that will guarantee a nearly constant pressure in the water vapor monitoring cell 252.

Again, the water vapor signal produced by the water vapor monitoring cell 252 includes two components in the time domain: an ambient water vapor signal and a hydrogen-derived water vapor signal. However, the above discussed flow switching will modulate the hydrogen-derived water vapor signal making it easier to separate. The more rapid the switching signal to the valves 254, 256, the more rapid the modulation and the easier the separation (provided the switching signal is still less (e.g., 10× less) than a measurement rate of the water vapor monitoring cell 252 to ensure resolution). In one embodiment, the switching signal is greater than 1 Hertz (Hz) (e.g., a 2 Hz square wave).

Figure 2C:
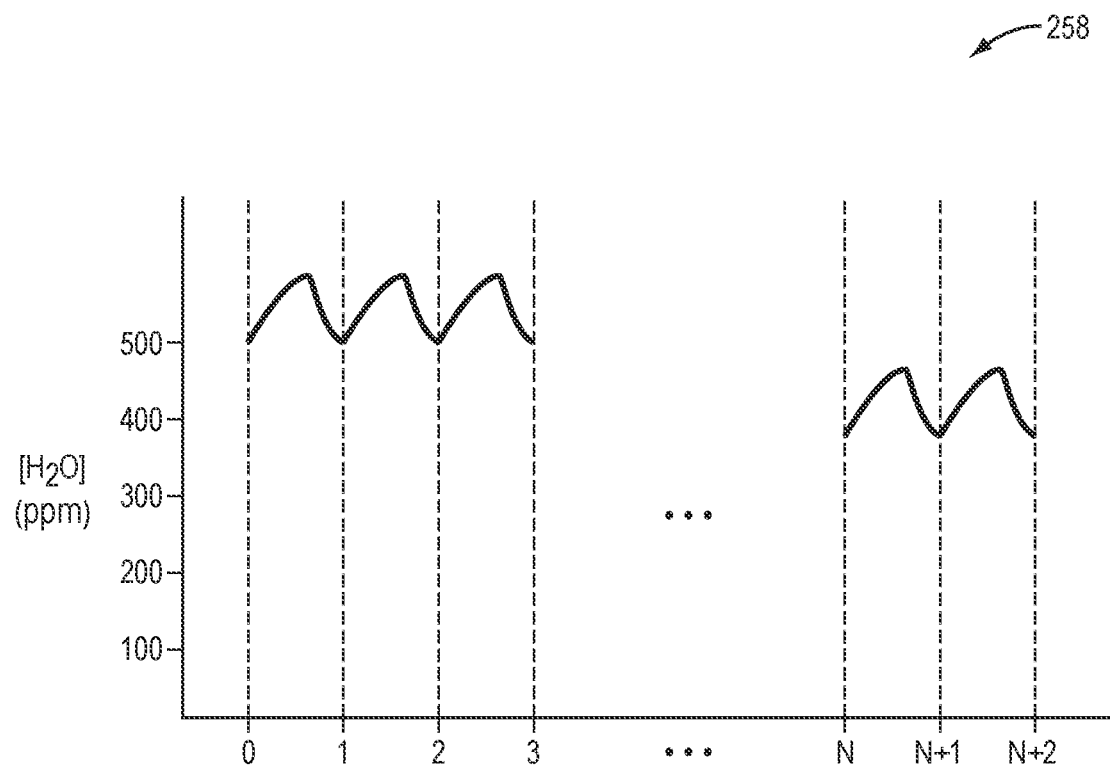
FIG. 2C is a graph illustrating an example water vapor signal having a hydrogen-derived water vapor component that has been rapidly modulated.

FIG. 2C is a graph 258 illustrating an example water vapor signal having a hydrogen-derived water vapor component that has been rapidly modulated. In this example, the rapidly modulated hydrogen-derived water vapor component corresponds to about 50 ppm of hydrogen and rides upon an ambient water vapor component that begins around 500 ppm and slowly decreases to about 400 ppm. The hydrogen-derived water vapor signal component is well separated in the time domain from the ambient water vapor component. In an idealized system, one would expect a 50 ppm square wave riding upon the ambient water vapor component. However, due to mixing and surface effects in real-world implementations, a damped square wave is more typical.

At step 270, the flows are reunited and both again pass through the gas dryer 222 (or more specifically the low-pressure segment thereof). An optional bypass path 262 may also be provided to avoid the low-pressure segment.

At step 280, the reunited flows pass through a vacuum pump 272 that pulls everything through the hydrogen detector 202 and out an outlet 274.

In parallel, at step 295, the water vapor signal from the water vapor monitoring cell 252 is received by the processor 282, which separates the water vapor signal in the time domain into the ambient water vapor signal and the modulated hydrogen-derived water vapor signal. The processor 282 determines a hydrogen signal that describes molecular hydrogen in the sample gas based on the modulated hydrogen-derived water vapor signal. In a simple implementation, while ignoring dampening of the modulation, the hydrogen signal can be determined as:

$$[H2]=[H2O]_{cc}-[H2O]_{bp}$$

where $[H2O]_{cc}$ is water vapor concentration measured when monitoring the chemical conversion flow and $[H2O]_{bp}$ is water vapor concentration measured when monitoring the bypass flow. In more complicated implementations, DSP techniques may be used. For example, the processor 282 may implement a digital lock-in amplifier to account for distortion caused by dampening effects. Any ambient water vapor fluctuations that are not completely suppressed by the gas dryer 222 will not be phase coherent with the modulation frequency and thereby can readily be suppressed.

Finally, at step 297, the processor 282 outputs the hydrogen signal, for example, storing it in a memory, passing it to another instrument, using it to generate a display in a user-interface of the hydrogen detector 202 itself, etc.

Despite diligent efforts to maintain the paths of the chemical conversion flow and the bypass flow identical in the example hydrogen detector 202 discussed in relation to FIGS. 2A-2B, minute differences caused by leaks, differing amounts of water adsorption or desorption on surfaces, or other factors may affect accuracy, such that in the absence of hydrogen in the sample gas there may be a non-zero differential water vapor signal (i.e., an offset). That is, in the absence of hydrogen in the sample gas a differential water vapor signal should be exactly zero, but in practice it may be a non-zero quantity erroneously indicating presence of a small amount of hydrogen (e.g., <1 ppm).

Typically, such a non-zero differential water vapor signal (i.e., offset) is stable. Accordingly, it could be measured for the given hydrogen detector, and subtracted from the water vapor signal during subsequent measurements to provide correction. While workable, such an instrument-specific approach may be inconvenient and it may be desirable to design a hydrogen detector in a manner that ensures a differential water vapor signal of zero.

Figure 3A:
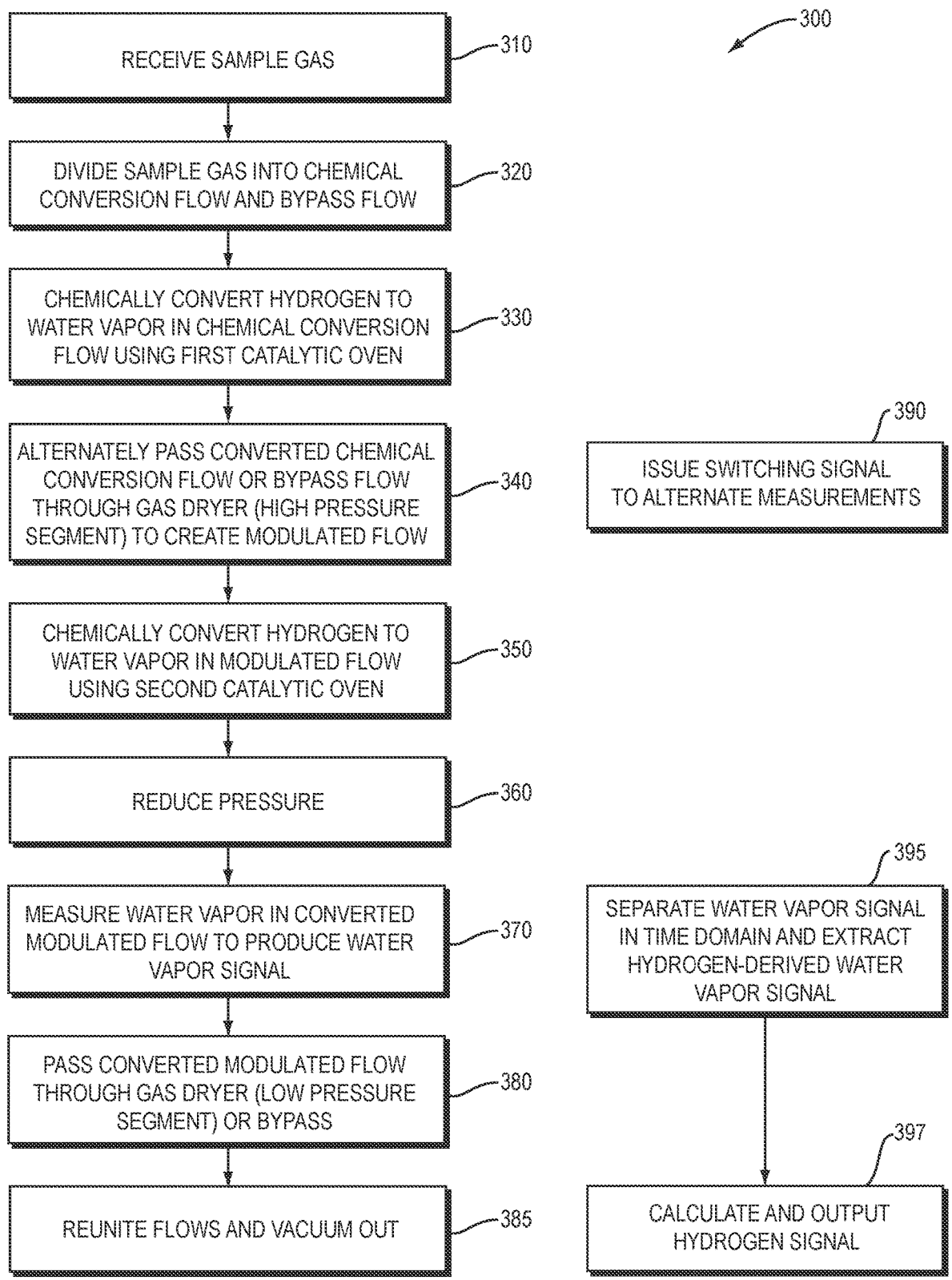
FIG. 3A is a flow diagram of an example sequence of steps for detecting molecular hydrogen according to a third embodiment.
Figure 3B:
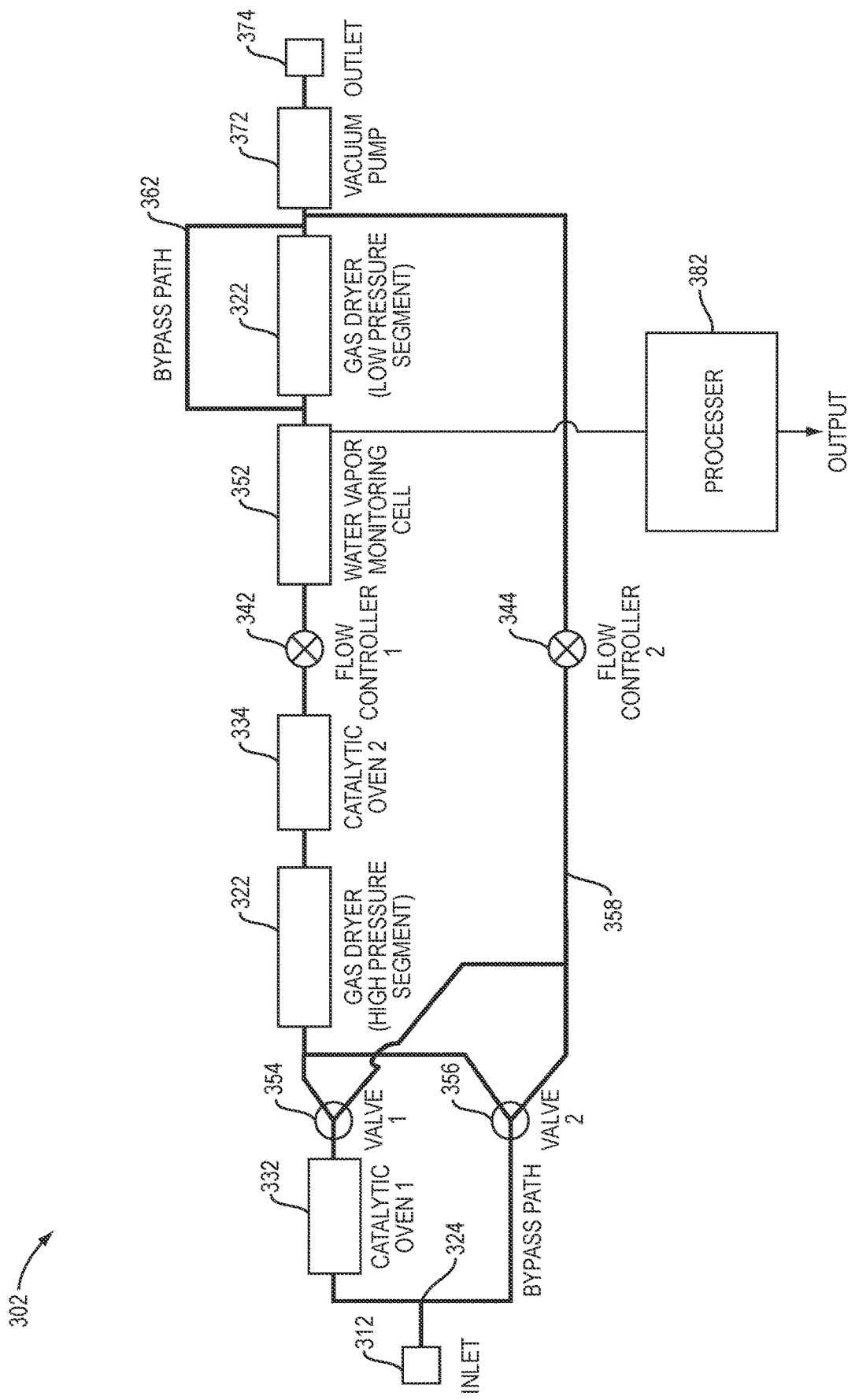
FIG. 3B is a block diagram of an example hydrogen detector with components that may implement the sequence of steps in FIG. 3A.

To such goal, the example hydrogen detector 202 discussed in relation to FIGS. 2A-2B may be modified by dividing the sample gas into the chemical conversion flow and the bypass flow before passing through the gas dryer, rather than after, and employing two catalytic ovens, rather than one. FIG. 3A is a flow diagram of an example sequence of steps 200 for detecting molecular hydrogen according to a third embodiment. FIG. 3B is a block diagram of an example hydrogen detector 302 with components that may implement the sequence of steps 300 in FIG. 3A. Where the steps and components of FIGS. 3A-3B are similar to those of FIGS. 1A-1B and 2A-2B they will be discussed again only briefly, and the reader is referred to the above discussion for more detail.

At step 310, an inlet 312 of the hydrogen detector 302 receives sample gas (e.g., atmospheric air) that includes ambient water vapor, molecular hydrogen and potentially hydrogen bearing molecules (including methane and NMHCs).

At step 320, sample gas from the inlet 312 is passed to a flow divider 324 that divides the sample gas in half, creating a first flow that is referred to herein as the "chemical conversion flow" and a second flow that is referred to herein as the "bypass flow." It should be noted that in contrast to the example hydrogen detector 202 discussed in relation to FIGS. 2A-2B, here the flow divider 324 is positioned before the gas dryer, or more specifically before a high-pressure segment thereof.

At step 330, the chemical conversion flow is passed to a first catalytic oven 332 that chemically converts hydrogen in the chemical conversion flow to water vapor. Like previously described catalytic ovens, the first catalytic oven 332 may include a hot (e.g., 200° C.) catalytic surface (e.g., a Pt surface) that rapidly and quantitatively converts hydrogen to water vapor, operating near atmospheric pressure.

At step 340, a gas dryer 322, or more specifically a high-pressure segment thereof, alternates between drying the converted chemical conversion flow or the bypass flow to produce a combined flow having alternating chemical conversion phases and bypass phases that is referred to herein as the "modulated flow." Again, the gas dryer 222 may be a Nafion® sulfonated tetrafluoroethylene based fluoropolymer-copolymer membrane gas dryer or another type of dryer. To cause such alternation, first and second valves (e.g., electronically-controlled three-way valves) 354, 356 may be employed. In one implementation, the first valve 354 receives the chemical conversion flow from the first catalytic oven 332 and directs it either to the gas dryer 322 (in its resting state) or to a bypass 358 around the gas dryer 322 and other downstream components (in its activated state). The second valve 356 receives the bypass flow from the inlet 312 and directs it either around the gas dryer 322 and other downstream components (in its resting state) or to the gas dryer 322 (in its activated state). The first and second valves 354, 356 may operate in response to a switching signal (e.g., a square wave).

In parallel steps, at step 390, a processor 382 is configured to issue the switching signal (e.g., a square wave) to the first and second valves 354, 356 to activate and deactivate them at a switching rate. In one embodiment, the switching rate is greater than 1 Hz (e.g., a 2 Hz), such that modulated flow has alternating chemical conversion phases and bypass phases with periods of less than 1 second (s) (e.g., less than 0.5 s). The switching signal may maintain constant flow and pressure through downstream components, such as the vapor monitoring cell 352.

As discussed above, the gas dryer 122 serves a role similar to a low pass filter in the field of electronics. Because of its placement after the first catalytic oven 332 it may serve to erase a non-zero differential water vapor signal. This is because any variations or drift resulting from leaks, differing amounts of water adsorption or desorption on surfaces, or other factors, typically will be smeared (i.e., dispersed) over a lengthy period of time (referred to herein as a "drift time"), for example, a period of time greater than 1 minute (min) (e.g., >2 mins), while the period of the chemical conversion phases and bypass phases of the modulated flow are typically short, for example, less than 1 second (s) (e.g., <0.5 s). Said differently, the switching rate will typically be significantly faster, for example, at least 5 times faster (e.g., >60 times faster) than the drift time. As such, when time domain separation is performed in later operations the variation or drift will be separated out, and any differences in water vapor concentration between the chemical conversion flow and the bypass flow erased.

One issue, however, is that placement of the gas dryer 322 in this location will also erase any hydrogen-derived water vapor signal produced by the first chemical conversion, such that without something more the detector 302 would not operate. To recover a hydrogen-derived water vapor signal, a second conversion of hydrogen to water vapor may be performed that produces hydrogen-derived water vapor from hydrogen in the bypass phases of the modulated flow.

At step 350, the modulated flow is passed to a second catalytic oven 334 that chemically converts hydrogen in the modulated flow to water vapor, producing a converted modulated flow. While hydrogen in the chemical conversion phases of the modulated flow was previously converted to water vapor (and any hydrogen-derived water vapor signal therefrom erased), hydrogen in the bypass phases of the modulated flow is still available for conversion in the second catalytic oven 334. Like previously described catalytic ovens, the second catalytic oven 334 may include a hot (e.g., 200° C.) catalytic surface (e.g., a Pt surface) that rapidly and quantitatively converts hydrogen to water vapor, operating near atmospheric pressure.

At step 360, the converted modulated flow from the second catalytic oven 334 is passed through a first flow controller 342 that reduces its pressure, and the bypass flow is passed through a second flow controller 344 that reduces its pressure. Again, to avoid water condensation these regions may be maintained at an elevated temperature (e.g., 30° C. or greater).

At step 370, the converted modulated flow is passed to a water vapor monitoring cell 352 that measures water vapor in the converted modulated flow to produce a water vapor signal. Again, the water vapor monitoring cell 352 may employ optical detection, for example, laser spectroscopy or NDIR absorption spectroscopy.

At step 380, the converted modulated flow is passed to the gas dryer 322, or more specifically the low-pressure segment thereof. An optional bypass path 362 may also be provided to avoid the low-pressure segment.

At step 385, the flows are reunited and passed through a vacuum pump 372 that pulls everything through the hydrogen detector 302 and out an outlet 374.

In parallel steps, at step 395, the water vapor signal from the water vapor monitoring cell 252 is received by a processor 382, which separates the water vapor signal in the time domain to extract the hydrogen-derived water vapor signal. As in the detector 202 of FIGS. 2A-2B, the active modulation produced by operation of the valves 354, 356 facilitates separation. A measurement rate that is significantly greater than the switching rate (e.g., a measurement rate at least 10× greater than the switching rate) and a switching rate that is significantly faster than the drift time (e.g., a switching rate at least 60× faster than the drift time) may be employed.

The processor 382 determines a hydrogen signal that describes molecular hydrogen in the sample gas based on the hydrogen-derived water vapor signal. In a simple implementation, while ignoring dampening, the hydrogen signal can be determined as:

$$[H2]=[H2O]_{bpmf}-[H2O]_{ccmf}$$

where $[H2O]_{bpmf}$ is water vapor concentration measured during the bypass flow phase of the converted modulated flow, and $[H2O]_{ccmf}$ is water vapor concentration measured during the chemical conversion phase of the converted modulated flow. In more complicated implementations, DSP techniques may be used. For example, the processor 382 may implement a digital lock-in amplifier to account for distortion caused by dampening effects.

Finally, at step 397, the processor 382 outputs the hydrogen signal, for example, storing it in a memory, passing it to another instrument, using it to generate a display in a user-interface of the hydrogen detector 302 itself, etc.

Operation of the various embodiments may be improved with various enhancements. In some enhanced embodiments, ambient water vapor fluctuations may be further suppressed by humidifying the sample gas to a predetermined relative humidity (e.g., 99%) using a humidifier (not shown in FIG. 1B, 2B or 3B) prior to passing the sample gas through the gas dryer 122, 222, 322. Humidifying the sample gas to a predetermined relative humidity will erase memory of the actual ambient water vapor concentration. The gas dryer 122, 222, 322 will reduce water vapor to a constant, stable level such that the ambient water vapor signal will not significantly vary even if actual ambient water vapor varies.

In further enhanced embodiments, hydrogen bearing molecules (including methane and NMHCs) in the sample gas that could be converted to water vapor and thereby produce an interfering signal are addressed. In some enhanced embodiments, hydrogen bearing molecules are suppressed by trapping using filter materials, membranes, molecular sieves, cryogenic traps and/or other trapping components. The trapping components may include pre-filters that reduce water vapor and carbon dioxide concentrations (e.g., to <1 ppm) to avoid saturation of the components intended to capture hydrogen bearing molecules. In some implementations, trapping components may be disposed between the gas dryer 122, 222, 322 and the water vapor monitoring cell 152, 252, 352. While trapping may be used with methane, trapping may be particularly well suited for suppressing hydrogen NMHCs since they are much stickier than hydrogen and are usually present in low concentrations.

In further enhanced embodiments, the catalytic oven 132, 232, 332, 334 may be tuned to selectively oxidize hydrogen while avoiding conversion of hydrogen bearing molecules to water vapor. Selective oxidation may be particularly well suited for suppressing methane since methane is relatively more difficult to oxidize than hydrogen, and thereby parameters may be selected for the catalytic oven 132, 232, 223, 334 that substantially oxidize one but not the other.

In still further enhanced embodiments, hydrogen bearing molecules in the sample gas may be compensated for by measuring hydrogen bearing molecule concentrations in the sample gas, calculating an amount of hydrogen bearing molecule-derived water vapor based on the measured hydrogen bearing molecule concentrations, and subtracting out hydrogen bearing molecule-derived water vapor from the water vapor signal. Compensation-based techniques may be particularly well suited for addressing methane. Such measurements used in compensation-based techniques may be collected, for example, by adapting the techniques of FIGS. 2A-2B or FIGS. 3A-3B. Total methane concentration may be measured in the bypass flow (e.g., using a methane gas detector (not shown in FIG. 2B)). In the chemical conversion flow, methane concentration that survives passage through the catalytic oven(s) 232, 332, 334 is also measured (e.g., again using a methane gas detector (not shown in FIG. 2B or FIG. 3B)). The difference between the total methane concentration and the surviving methane concentration indicates the quantity of methane oxidized in the catalytic oven(s) 232, 332, 334. The processor 282, 382 may determine a hydrogen signal that describes molecular hydrogen in the sample gas by subtracting out water vapor derived from methane oxidation. Each oxidized methane molecule will produce two water molecules, whereas oxidized hydrogen molecules will produce one water molecule. In more complicated implementations, the hydrogen signal can be determined using DSP techniques (e.g., a digital lock-in amplifier) to account for distortion caused by dampening effects.

In summary, the above description provide example techniques for rapid, sensitive detection of molecular hydrogen. It should be understood that various adaptations, modifications, and extensions may be made to suit various design requirements and parameters. For example, the techniques may be extended to determine hydrogen eddy covariance flux. An anemometer may be added to the hydrogen detector 102, 202, 302 to measure air movement. The processor 182, 282, 382 may be adapted to determine hydrogen eddy covariance flux based on correlation between the measurement of air movement and the water vapor signal.

Above all it should be understood that the above descriptions are meant to be taken only by way of example and the invention is not limited to the specific details of the example embodiments disclosed. What is claimed is:

The invention claimed is:

1. A method for detecting molecular hydrogen, comprising:
receiving sample gas that includes ambient water vapor and hydrogen;
dividing the sample gas into a chemical conversion flow and a bypass flow;
performing a first chemical conversion of hydrogen in the chemical conversion flow to water vapor;
alternating between drying the converted chemical conversion flow or the bypass flow to produce a modulated flow;
performing a second chemical conversion of hydrogen in the modulated flow to water vapor;
measuring water vapor in the converted modulated flow to produce a water vapor signal;
separating the water vapor signal to extract a hydrogen-derived water vapor signal; and
outputting a hydrogen signal that describes molecular hydrogen in the sample gas based on the hydrogen-derived water vapor signal.

2. The method of claim 1 wherein the alternating comprises:
alternately passing, by one or more valves, the converted chemical conversion flow or the bypass flow to a segment of a gas dryer.

3. The method of claim 2, wherein the gas dryer is a sulfonated tetrafluoroethylene based fluoropolymer-copolymer membrane gas dryer.

4. The method of claim 2, wherein the alternating maintains constant flow through the segment of the gas dryer.

5. The method of claim 1, wherein the performing the first chemical conversion comprises heating the chemical conversion flow in a first catalytic oven, and the performing the second chemical conversion comprises heating the modulated flow in a second catalytic oven.

6. The method of claim 1, wherein the ambient water signal drifts according to a drift time, and the alternating is performed at a switching rate that is at least 5 times faster than the drift time.

7. The method of claim 1, wherein the measuring is performed at a measurement rate and the alternating is performed at a switching rate that is at least 10 times less than the measurement rate.

8. The method of claim 1, wherein the measuring is performed by optically detecting water vapor using laser spectroscopy or non-dispersive infrared (NDIR) absorption spectroscopy.

9. The method of claim 1, further comprising:
humidifying the sample gas to a predetermined relative humidity.

10. The method of claim 1, further comprising:
compensating for hydrogen bearing molecules in the sample gas by measuring hydrogen bearing molecule concentrations in the sample gas, calculating an amount of hydrogen bearing molecule-derived water vapor based on the measured hydrogen bearing molecule concentrations, and subtracting out hydrogen bearing molecule-derived water vapor from the water vapor signal.

11. A molecular hydrogen detector, comprising:
an inlet configured to receive sample gas that includes ambient water vapor and hydrogen;
a flow divider configured to divide the sample gas into a chemical conversion flow and a bypass flow;
a first catalytic oven configured to chemically convert hydrogen in the chemical conversion flow to water vapor;
one or more valves configured to alternately pass either the converted chemical conversion flow or the bypass flow;
a gas dyer having a segment configured to alternately receive either the converted chemical conversion flow or the bypass flow and produce a modulated flow;
a second catalytic oven configured to chemically convert hydrogen in the modulated flow to water vapor;
a water vapor monitoring cell configured to measure water vapor in the converted modulated flow to produce a water vapor signal; and
a processor configured to separate the water vapor signal into an ambient water vapor signal and a hydrogen-derived water vapor signal, and to output a hydrogen signal that is based on the hydrogen-derived water vapor signal to describe molecular hydrogen in the sample gas.

12. The molecular hydrogen detector of claim 11, wherein the one or more valves comprise:
a first valve configured to selectively direct the chemical conversion flow to either the segment of the gas dryer or to bypass the segment of the gas dryer; and
a second flow valve configured to selectively direct the bypass flow to either the segment of the gas dyer to bypass the segment of the gas dryer,
wherein the processor is configured to activate and deactivate the first valve and the second valve to cause the segment of the gas dryer to alternately dry the converted chemical conversion flow or the bypass flow to produce the modulated flow.

13. The molecular hydrogen detector of claim 11, wherein the one or more valves are configured to maintain constant flow through the segment of the gas dryer.

14. The molecular hydrogen detector of claim 11, wherein the gas dryer is a sulfonated tetrafluoroethylene based fluoropolymer-copolymer membrane gas dryer.

15. The molecular hydrogen detector of claim 11, wherein the ambient water signal drifts according to a drift time, and the one or more valves are configured to alternately pass either the converted chemical conversion flow or the bypass flow at a switching rate that is at least 5 times faster than the drift time.

16. The molecular hydrogen detector of claim 11, wherein the water vapor monitoring cell is configured to measure the converted modulated flow at a measurement rate and the one or more valves are configured to alternately pass the converted chemical conversion flow or the bypass flow at a switching rate that is at least 10 times less than the measurement rate.

17. The molecular hydrogen detector of claim 11, wherein the water vapor monitoring cell comprises a laser spectrometer or a non-dispersive infrared (NDIR) absorption spectrometer.

18. The molecular hydrogen detector of claim 11, further comprising:
a humidifier disposed between the inlet and the first catalytic oven and configured to bring the sample gas to a predetermined relative humidity.

19. The molecular hydrogen detector of claim 11, further comprising:
a monitor configured to measure hydrogen bearing molecule concentrations in the sample gas,
wherein the processor is configured to compensate for hydrogen bearing molecules in the sample gas by calculating an amount of hydrogen bearing molecule-derived water vapor based on the measured hydrogen bearing molecule concentrations and subtracting out hydrogen bearing molecule-derived water vapor from the water vapor signal.

20. A molecular hydrogen detector, comprising:
means for receiving sample gas that includes ambient water vapor and hydrogen;
means for dividing the sample gas into a chemical conversion flow and a bypass flow;
first means for chemically converting hydrogen in the chemical conversion flow to water vapor;
means for alternately passing either the converted chemical conversion flow or the bypass flow;
means for producing a modulated flow in which both differences in water vapor concentration between the chemical conversion flow and the bypass flow and hydrogen-derived water vapor produced by the first chemical conversion has been erased;
second means for chemically converting hydrogen in the modulated flow to water vapor;
means for measuring water vapor in the converted modulated flow to produce a water vapor signal; and
means for separating the water vapor signal to extract a hydrogen-derived water vapor signal, and for outputting a hydrogen signal that is based on the hydrogen-derived water vapor signal to describe molecular hydrogen in the sample gas.

* * * * *